(12) United States Patent
Wieland et al.

(10) Patent No.: US 11,129,628 B2
(45) Date of Patent: Sep. 28, 2021

(54) TARGETING ADJUSTMENT

(71) Applicant: Stryker European Operations Holdings LLC, Kalamazoo, MI (US)

(72) Inventors: Manfred Wieland, Kiel (DE); Ole Prien, Kiel (DE)

(73) Assignee: Stryker European Operations Holdings LLC, Kalamazoo, MI (US)

(*) Notice: Subject to any disclaimer, the term of this patent is extended or adjusted under 35 U.S.C. 154(b) by 224 days.

(21) Appl. No.: 16/506,448

(22) Filed: Jul. 9, 2019

(65) Prior Publication Data

US 2019/0365392 A1     Dec. 5, 2019

Related U.S. Application Data

(62) Division of application No. 14/896,116, filed as application No. PCT/EP2014/060610 on May 23, 2014, now Pat. No. 10,390,844.

(30) Foreign Application Priority Data

Jun. 7, 2013  (WO) ................. PCT/EP2013/061831

(51) Int. Cl.
*A61B 17/58*     (2006.01)
*A61B 17/60*     (2006.01)
(Continued)

(52) U.S. Cl.
CPC .......... *A61B 17/1725* (2013.01); *A61B 17/72* (2013.01); *A61B 17/86* (2013.01);
(Continued)

(58) Field of Classification Search
None
See application file for complete search history.

(56) References Cited

U.S. PATENT DOCUMENTS

| | | |
|---|---|---|
| 4,135,505 A | 1/1979 | Day et al. |
| 4,541,424 A | 9/1985 | Grosse et al. |

(Continued)

FOREIGN PATENT DOCUMENTS

| | | |
|---|---|---|
| DE | 20211806 U1 | 10/2002 |
| EP | 0354395 A2 | 2/1990 |

(Continued)

OTHER PUBLICATIONS

Gamma3™, Distal Targeting Device R2.0, Operative Technique, Stryker Osteosynthesis, Germany, 2006, 32 pgs.

(Continued)

*Primary Examiner* — Sameh R Boles
(74) *Attorney, Agent, or Firm* — Lerner, David, Littenberg, Krumholz & Mentlik, LLP (57) ABSTRACT

A targeting system for aligning an axis of a targeting sleeve and a bore in a distal end portion of an intramedullary nail is proposed, the targeting device comprising a distal targeting arm with a first end being configured to be coupled to a trailing end of an intramedullary nail, an adjusting device, the adjusting device being configured to be coupled to the distal targeting arm. The adjusting device may comprise an adjusting element and a nail follower including two targeting holes each being configured to receive a sleeve assembly. The adjusting element may cooperate with the nail follower such that the positions of the two targeting holes are adjustable so as to correspond to respective locking holes at a leading end of the intramedullary nail, even when the nail is bent.

20 Claims, 10 Drawing Sheets

(51) Int. Cl.
*A61F 2/00* (2006.01)
*A61B 17/17* (2006.01)
*A61B 90/00* (2016.01)
*A61B 17/72* (2006.01)
*A61B 17/86* (2006.01)
*A61B 17/90* (2006.01)
*A61B 17/92* (2006.01)

(52) U.S. Cl.
CPC .......... *A61B 90/39* (2016.02); *A61B 17/1703* (2013.01); *A61B 17/7208* (2013.01); *A61B 17/921* (2013.01); *A61B 2017/90* (2013.01); *A61B 2090/3966* (2016.02)

(56) References Cited

U.S. PATENT DOCUMENTS

| | | | |
|---|---|---|---|
| 4,667,664 A | | 5/1987 | Taylor et al. |
| 4,865,025 A | | 9/1989 | Buzzi et al. |
| 4,881,535 A | * | 11/1989 | Sohngen ............ A61B 17/1725 606/98 |
| 4,917,111 A | | 4/1990 | Pennig et al. |
| 4,969,889 A | | 11/1990 | Greig |
| 5,031,203 A | | 7/1991 | Trecha |
| 5,122,146 A | | 6/1992 | Chapman et al. |
| 5,433,720 A | | 7/1995 | Faccioli et al. |
| 5,478,343 A | | 12/1995 | Ritter |
| 5,630,805 A | | 5/1997 | Ternamian et al. |
| 5,713,902 A | | 2/1998 | Friedl |
| 6,036,696 A | | 3/2000 | Lambrecht et al. |
| 6,039,742 A | | 3/2000 | Krettek et al. |
| 6,214,013 B1 | | 4/2001 | Lambrecht et al. |
| 6,231,576 B1 | | 5/2001 | Frigg et al. |
| 6,514,253 B1 | | 2/2003 | Yao |
| 6,520,969 B2 | | 2/2003 | Lambrecht et al. |
| 6,656,189 B1 | | 12/2003 | Wilson et al. |
| 6,932,818 B2 | | 8/2005 | Behrens |
| 7,077,847 B2 | | 7/2006 | Pusnik et al. |
| 7,175,631 B2 | | 2/2007 | Wilson et al. |
| 7,481,815 B2 | | 1/2009 | Fernandez |
| 8,231,629 B2 | | 7/2012 | Lemer et al. |
| 8,685,034 B2 | | 4/2014 | Giersch et al. |
| 8,715,282 B2 | | 5/2014 | Pool |
| 8,864,771 B2 | | 10/2014 | Buscher et al. |
| 2003/0212405 A1 | | 11/2003 | Choi |
| 2004/0039393 A1 | | 2/2004 | Robioneck et al. |
| 2004/0167533 A1 | | 8/2004 | Wilson et al. |
| 2005/0177175 A1 | | 8/2005 | Johnstone |
| 2006/0030859 A1 | | 2/2006 | Gotfried |
| 2006/0064106 A1 | | 3/2006 | Fernandez |
| 2006/0098851 A1 | | 5/2006 | Shoham et al. |
| 2008/0058829 A1 | | 3/2008 | Buscher et al. |
| 2008/0281330 A1 | | 11/2008 | Ferrante et al. |
| 2012/0303038 A1 | | 11/2012 | Durante et al. |
| 2013/0110119 A1 | | 5/2013 | Atkinson et al. |
| 2014/0052132 A1 | | 2/2014 | Matityahu et al. |

FOREIGN PATENT DOCUMENTS

| | | |
|---|---|---|
| EP | 1099413 | 5/2001 |
| EP | 1356777 | 10/2003 |
| EP | 2049025 A1 | 4/2009 |
| WO | 03/065907 | 8/2003 |
| WO | 2012162608 A1 | 11/2012 |

OTHER PUBLICATIONS

Gamma3™, Long Nail R2.0, Operative Technique, Stryker Osteosynthesis, Germany, 2006, 52 pgs.
H. P. Granhed, A new technique for distal screw insertion for locked nailing, Acta Orthop vol. 69 (3), 1998, pp. 320-321.
International Search Report and Written Opinion for PCT/EP2013/061831 dated Mar. 13, 2014.
International Search Report for Application No. PCT/EP2014/060610 dated Nov. 11, 2014.
Japanese Publication, 2000 (one shot guide).
One Shot Device, Gamma Locking Nail Instruments, Operative Technique, Stryker Trauma, 2000.
Operative Technique, One shot Device, pp. 25 and 34, date not known.

* cited by examiner

TARGETING ADJUSTMENT

CROSS-REFERENCE TO RELATED APPLICATIONS

The present application is a divisional of U.S. patent application Ser. No. 14/896,116 filed Dec. 4, 2015, now U.S. Pat. No. 10,390,844, which is a national phase entry under 35 U.S.C. § 371 of International Application No. PCT/EP2014/060610 filed May 23, 2014, published as International Publication No. WO 2014/195147 A1, which claims priority from International Application No. PCT/EP2013/061831 filed Jun. 7, 2013, published as International Publication No. WO 2014/194965 A1, all of which are hereby incorporated herein by reference.

FIELD OF THE DISCLOSURE

The invention relates to a distal targeting device, in particular to a device for adjusting an axis of a sleeve for inserting a locking screw relative to a bore axis in a distal end portion of an intramedullary nail. Furthermore, the invention relates to a method for operating the device.

BACKGROUND INFORMATION

An intramedullary nail may be implanted in a fractured bone, such as a tibia or a femur, the implantation being such that the nail extends distally and proximally with respect to the fracture, in reinforcement of fractured parts of the bone that have been re-aligned or merely are to be held in alignment for the course of healing repair.

Intramedullary nails of the character indicated are usually prepared with two spaced parallel holes that extend diametrically across the nail near the distal end of the nail and may be prepared with two spaced holes of similar nature, but not necessarily parallel, near the proximal end of the nail. These holes are formed to accept bone screws, and when the nail has been installed, its bone-screw holes are said to be "blind" in terms of the bone-drilling alignment that must be achieved.

The problem has always been one of assuring correct alignment for drilling a hole to accept a bone screw driven through bone for anchoring passage through the intramedullary nail. One of the problems of locating a bone-screw hole in an installed intramedullary nail is the practical fact that the nail may have undergone a slight bend in the course of implantation, so that such holes at the distal end of the nail no-longer have precisely the same location with respect to the proximal end, as was the case prior to nail implantation.

EP 2 049 025 A1 describes a targeting device for targeting a cross bore in a bone nail, the targeting device comprising an arm member coupled to an end portion of the bone nail and an aiming portion forming part of the arm member extending parallel to a longitudinal axis of the bone nail. An adjustable aiming device is mounted on the aiming portion, the adjustable device having a guide bore alignable with the cross bore in the nail. The adjustable device is moveable with respect to the aiming portion in a direction perpendicular to a plane containing both the nail longitudinal axis and central axis of the cross bore. A target indicator is mounted on the adjustable aiming device. Here, the adjustment is performed based on an x-ray image generated when the nail is already inserted into the bone.

SUMMARY OF THE INVENTION

An object may be to provide an improved device and a method for targeting a screw hole in a distal end portion of an intramedullary nail, i.e. aligning an axis of a targeting sleeve with an axis of the screw hole, in particular allowing a compensation of a bending of the nail.

This is achieved by the subject-matter of the respective independent claims. Further embodiments are described in the dependent claims.

In general, a targeting system for aligning an axis of a targeting sleeve and a bore in a distal end portion of an intramedullary nail comprises a distal targeting arm with a first end being configured to be coupled to a proximal end, i.e. a trailing end of an intramedullary nail, an adjusting device, the adjusting device being configured to be coupled to the distal targeting arm. The adjusting device may comprise an adjusting element and a nail follower including two targeting holes each being configured to receive a sleeve assembly. The adjusting element may cooperate with the nail follower such that the positions of the two targeting holes are adjustable so as to correspond to respective locking holes at a distal end, i.e. a leading end of the intramedullary nail, even when the nail is bent.

According to an embodiment, the adjusting element of the targeting device may comprise at least one screw having a thread which engages with a threaded hole in the nail follower.

Assuming that the targeting holes are in positions which align with the locking holes in the nail, i.e. the nail follower is in a neutral position, when the distal targeting arm is coupled to the proximal end of the not yet inserted intramedullary nail, and further assuming that the nail is slightly bent in response to forces applied by the bone onto the already inserted nail, the adjusting element is configured to force the nail follower from the neutral position to a position which corresponds to the position of the nail portion of the bent nail including the locking holes.

It will be understood that also other mechanical means, for example a cam mechanism with a lever, may be provided to achieve the intended function of adjusting of the position of the nail follower.

According to an embodiment, a cam mechanism may be provided, including a curved slot and a pin engaging the slot, wherein the nail follower may comprise the pin and the slot may be provided in a housing of the adjustment device. Such a cam mechanism allows controlling the position of the two targeting holes in the nail follower in a specific way within two dimensions. For example, the adjusting element may force the nail follower in a first direction, whereas the cam mechanism simultaneously forces the nail follower in a second direction being perpendicular to the first direction.

In one embodiment, the adjusting element of the targeting device comprises two screws wherein a first screw includes a first thread with a first pitch and a second screw includes a second thread with a second pitch, wherein the first pitch differs from the second pitch and wherein the first and second screws are coupled by a gear system of at least two intermeshing gears with a gear ratio of 1:1, i.e. the first and second screws may simultaneously rotate by the same circumferential angle when the adjusting element is operated.

According to a further embodiment, the adjusting element of the targeting device comprises two screws with equal pitches, wherein the two screws are coupled by a gear system with a gear ratio different from 1:1, i.e. the two screws may simultaneously rotate by different circumferential angles relative to each other, when the adjusting element is operated.

Otherwise, the nail follower may be configured to be deformed so as to adjust the position of the targeting holes.

Such deformation may be caused by at least one screw as described in the previous embodiments.

According to an embodiment, a first end portion of the nail follower may be coupled to the targeting arm by a first pivot axis and a second end portion of the nail follower may be coupled to the targeting arm by a second pivot axis, and the nail follower may be configured to be deformed so as to adjust the position of the targeting holes by means of an adjusting device being arranged between the two pivot axes. Due to the pivot axes, it may be possible to achieve a continuous bending of the nail follower along its length, i.e. without an inversion of the bending direction.

It is noted that it is intended to displace the first one of the two targeting holes by a length which is different to the length by which the second one of the targeting holes is displaced. It will be understood that each of the above mentioned concepts alone as well as any combination thereof is suitable to achieve this.

According to an embodiment, the position of a first one of the targeting holes is displaced by a first length and the position of the second one of the targeting holes is displaced by a second length, when the adjusting element is operated, wherein the first length may be 5 to 15 percent larger than the second length, in particular 8 to 12 percent larger than the second length, and for example 10 percent larger than the second length.

According to an embodiment, the adjusting element may comprise two screws, wherein a first one of the two screws may rotate in an opposite direction relative to a second one of the two screws, when the adjusting device is operated.

According to an embodiment, a first threaded bore in the nail follower may be arranged adjacent of a first one of the two targeting holes and a second threaded bore in the nail follower may be arranged adjacent of a second one of the two targeting holes, with the axes of the threaded bores being oriented transverse to the axes of the targeting holes.

According to an embodiment, the nail follower may comprise a first member including a first one of the targeting holes and a second member including a second one of the targeting holes, wherein the first member and the second member may be movable relative to each other so as to adjust the position of the targeting holes.

According to a further embodiment, the adjusting device of the targeting device may further comprise a housing including a plurality of radio-opaque markers with a distribution allowing a determination of a 3D-orientation of the housing based on a 2D x-ray image.

According to another aspect, a method of operating the targeting device as described above may comprise the steps of receiving an x-ray image generated in a plane defined by at least one of the axes of the targeting holes and a main axis of an intramedullary nail to which the targeting device is coupled, determining a deviation of the axis of the targeting hole and an axis of a related one of two screw holes in the intramedullary nail based on the received x-ray image, and operating the adjusting element of the adjusting device so as to align the axis of the targeting hole with the axis of the related screw hole, thereby also aligning the axis of the other one of the targeting holes with the respectively related one of the two screw holes in the intramedullary nail.

According to another embodiment, the method may further comprise the step of adjusting an x-ray imaging device like a C-arm based X-ray imaging device so as to generate an x-ray image in the plane defined by the axis of the targeting sleeve and the main axis of the intramedullary nail. The x-ray imaging device may further be adjusted so as to generate an x-ray image with an angle relative to the intramedullary nail of 50 to 70 degree, for example of 60 degrees.

According to a further embodiment, the method does not include any step of inserting an intramedullary nail into a bone, leading to a situation in which an intramedullary nail is positioned in a bone, in so far as the step constitutes a treatment of a human or animal body by surgery.

It has to be noted that embodiments of the invention are described with reference to different subject-matters. In particular, some embodiments are described with reference to method-type claims, whereas other embodiments are described with reference to apparatus-type claims. However, a person skilled in the art will gather from the above and the following description that, unless otherwise notified, in addition to any combination of features belonging to one type of subject-matter, also any combination of features relating to different subject-matters is considered to be disclosed with this application.

These and other objects, features and advantages of the exemplary embodiments of the present invention will become apparent upon reading the following detailed description of exemplary embodiments, when taken in conjunction with the appended claims.

BRIEF DESCRIPTION OF THE DRAWINGS

The invention will now be detailed by way of exemplary embodiments with reference to the attached drawings.

FIG. 3a is a side view of an adjusting device according to the first embodiment.

FIG. 3b is a sectional view of the adjusting device of FIG. 3a.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures, as defined by the appended claims.

DETAILED DESCRIPTION OF EXEMPLARY EMBODIMENTS

Figure 1:
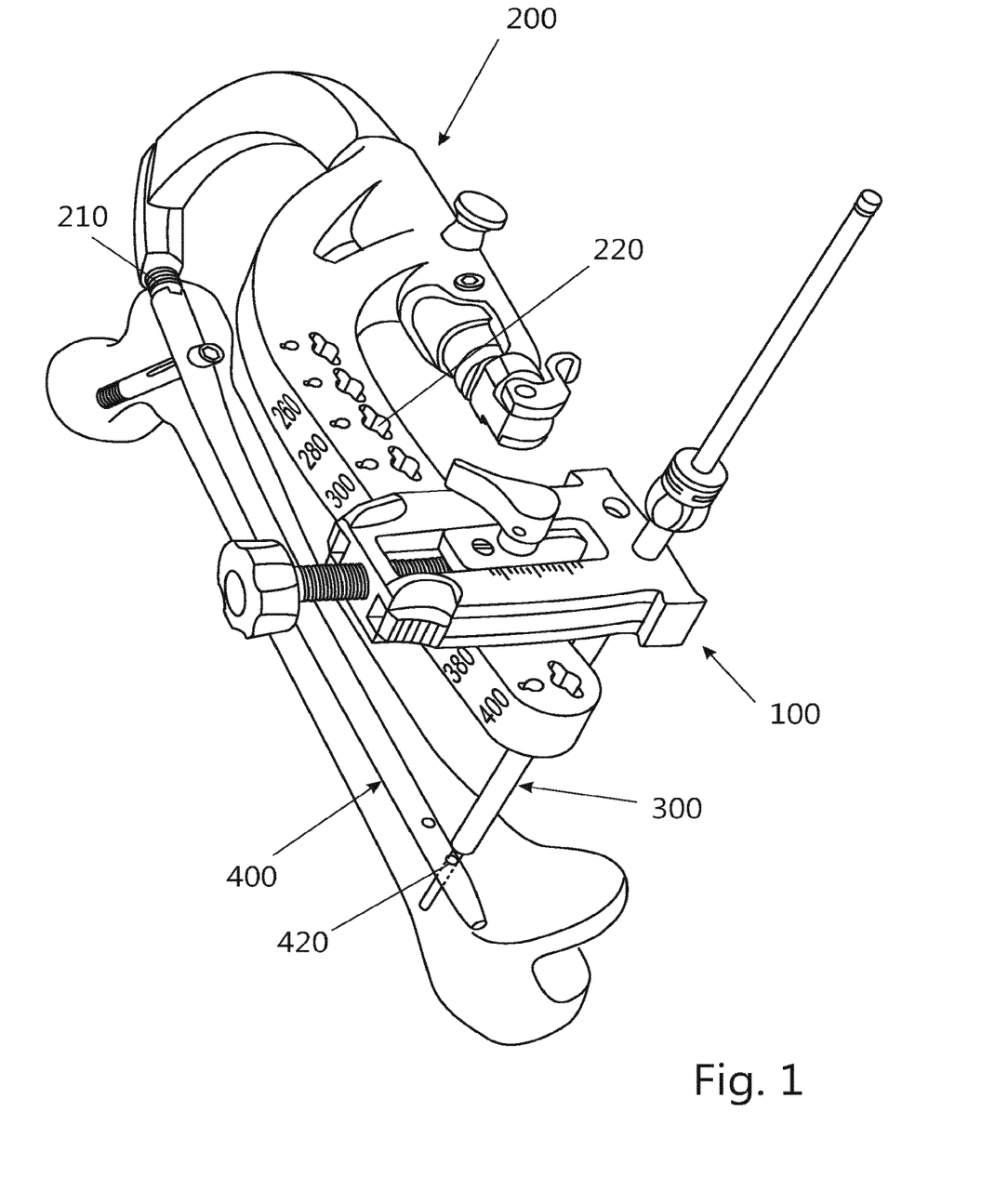
FIG. 1 is an isometric visualization of a targeting system for an intramedullary nail.

FIG. 1 provides an isometric illustration of an embodiment of a targeting system for an intramedullary nail, the system comprising an adjusting device 100 and a targeting arm 200. An intramedullary nail 400 is coupled at a proximal end thereof with a first end 210 of the targeting arm. The targeting arm 200 further comprises holes 220 as receipts for the adjusting device 100. The targeting arm may comprise a plurality of holes 220 so that the adjusting device may be coupled to the targeting arm at different positions so as to adapt the position of the targeting holes of the adjusting device to the positions of the locking holes in the distal end portion of different intramedullary nails with different lengths.

Further shown in FIG. 1 is a sleeve assembly 300 which extends through one of the targeting holes in the adjusting device 100. Here, the axis of the sleeve assembly 300 is aligned with the axis of a first locking hole 420 in the nail 400. The sleeve assembly may comprise an outer tissue protection sleeve, a drill sleeve as well as a trocar.

Figure 2:
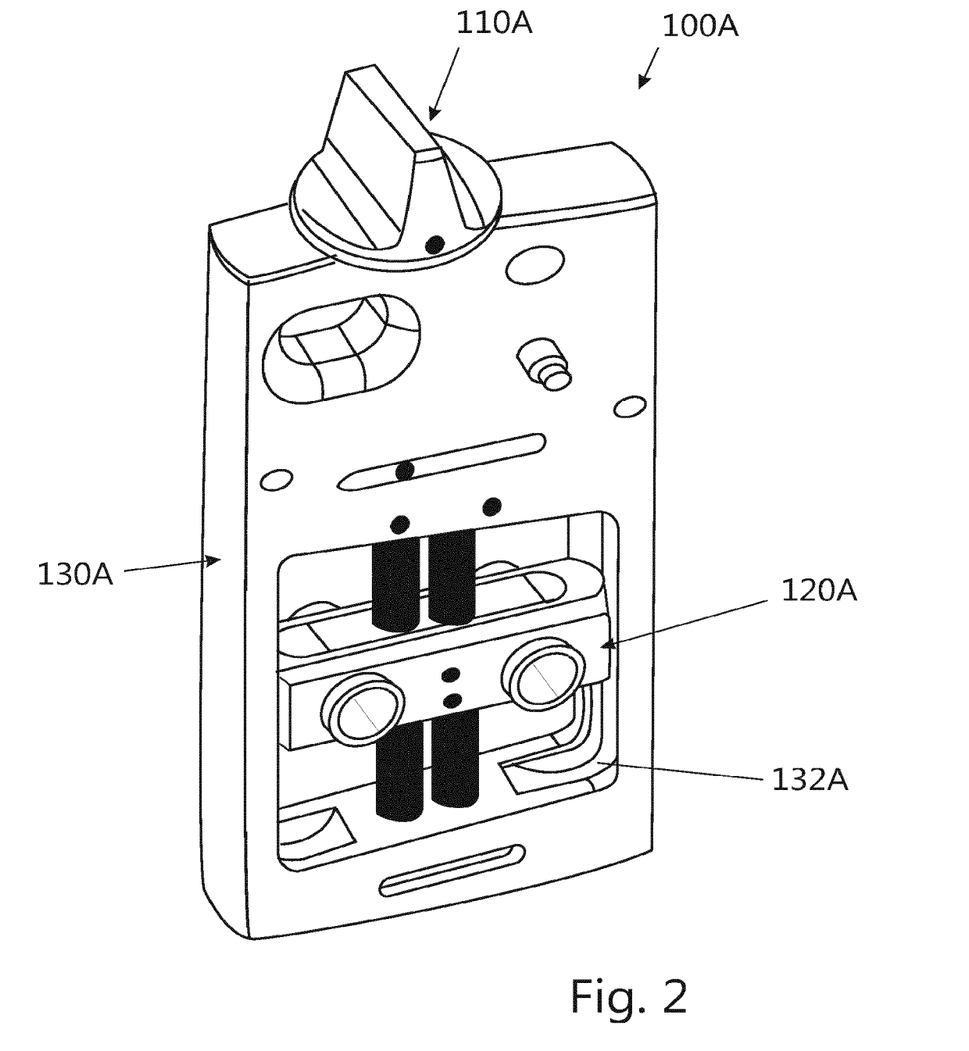
FIG. 2 shows an isometric view of an adjusting device according to a first embodiment.

FIG. 2 is an isometric illustration of an adjusting device 100A. The adjusting device 100A generally comprises an adjusting element 110A, a nail follower 120A and a housing 130A. These elements will be described in detail based on different embodiments in conjunction with the following figures.

Figures 3A, 3B:
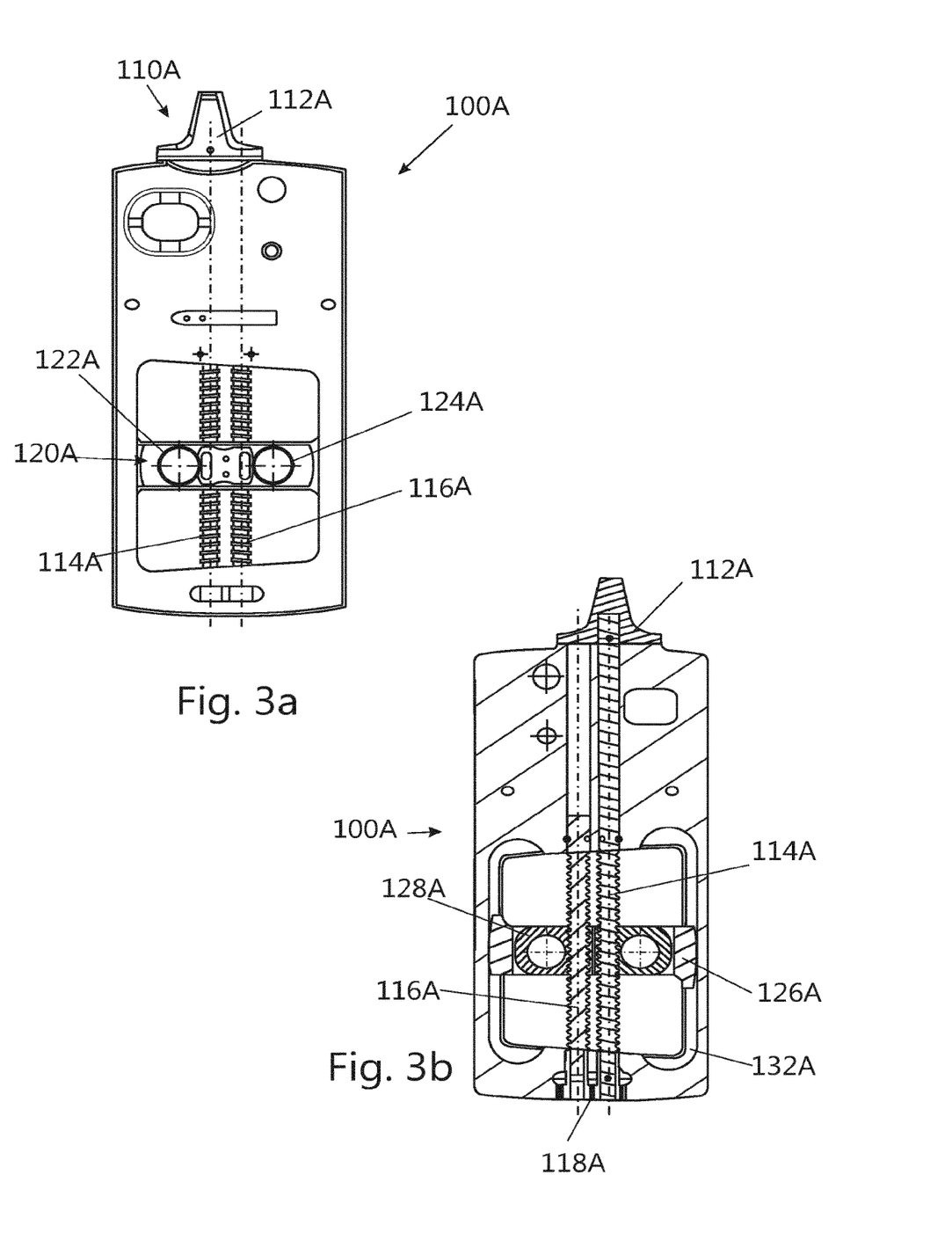

FIGS. 3a and 3b show an embodiment of an adjusting device 100A, with FIG. 3a being a plane view of the front side and FIG. 3b being a sectional view of the back side of the adjusting device 100A. In this embodiment, the adjusting element 110A comprises a knob 112A, a first screw 114A, a second screw 116A as well as a mechanical gear 118A. The knob 112A is arranged at the top of the housing of the adjusting device 100A and is coupled with the first screw 114A so that the first screw can be rotated by operating the knob. The rotational movement of the first screw 114A is transmitted by means of the gear system 118A from the first screw to the second screw 116A so that the screws are coupled so as to rotate simultaneously. According to the embodiment, the first screw 114A may have a right-hand thread and the second screw 116A may have a left-hand thread. The gear system 118A may have two intermeshing gears or tooth wheels engaging each other.

The first and second screws engage with respective threaded holes in the nail follower 120A. According to the embodiment, the pitch of the first thread may be larger than the pitch of the second thread. With the right-hand thread rotating in an opposite direction as the left-hand thread, and with the two different pitches, it can be achieved that the nail follower will be moved so that the first targeting hole 122A is displaced by a greater length as the second targeting hole 124A.

The nail follower 120A comprises a nail follower body 126A and two nail follower members 128A. The nail follower body includes slightly curved outer edges which may engage in a groove 132A formed in the housing 130A of the adjusting device. The curved outer edges allow a movement of the nail follower body so that the nail follower body is canted or angled with respect to the parallel screw axis by the action of the two screws. The two nail follower members 128A are provided in the nail follower body 126A, wherein the nail follower members comprise straight contact surfaces, respectively, so that the nail follower members may slide along each other due to an action of the two screws. The threaded bores for accommodating the screws 114A, 116A are provided in the nail follower members 128A, respectively.

Figure 4:
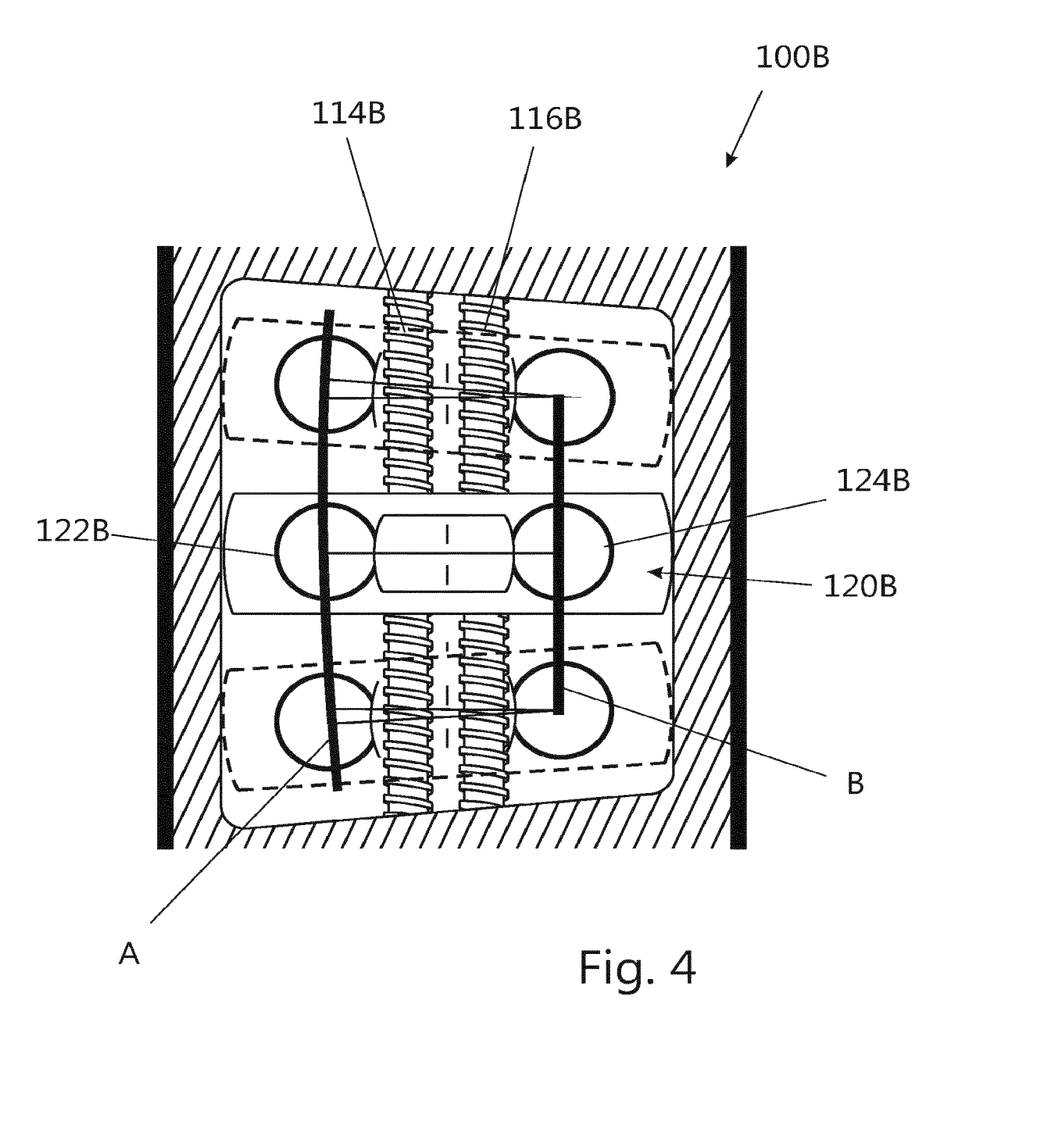
FIG. 4 is a detail view of a mid-portion of an adjusting device according to a second embodiment.

The aspect, that the first targeting hole is displaced differently relative to the second targeting hole is further illustrated in FIG. 4 which is a detailed view of the mid-section of the adjusting device 100B particularly showing the engagement of the first screw 114B and the second screw 116B with the nail follower 120B. For illustrative purposes, and arc section denoted with A is drawn in to show the path of the first targeting hole 122B, when the nail follower 120B is moved. On the other hand, a substantially straight line denoted with B is drawn in to show the path of the second targeting hole 124B.

It is noted that FIG. 4 shows an embodiment in which the first and second screws 114B, 116B both include the same threads, i.e. both include right-hand or left-hand threads. These screws may be coupled by a gear which transmits a rotation from the first screw 114B to the second screw 116B such that the screws rotate in the same direction and simultaneously. This might be achieved by means of a tooth belt or by a sequence of tooth wheels. To achieve the different displacement of the targeting holes, as shown in FIG. 4, the pitches of the two screws may differ from each other or alternatively a gear ratio different from 1:1 may be realized by the gear between the two screws.

Figure 5:
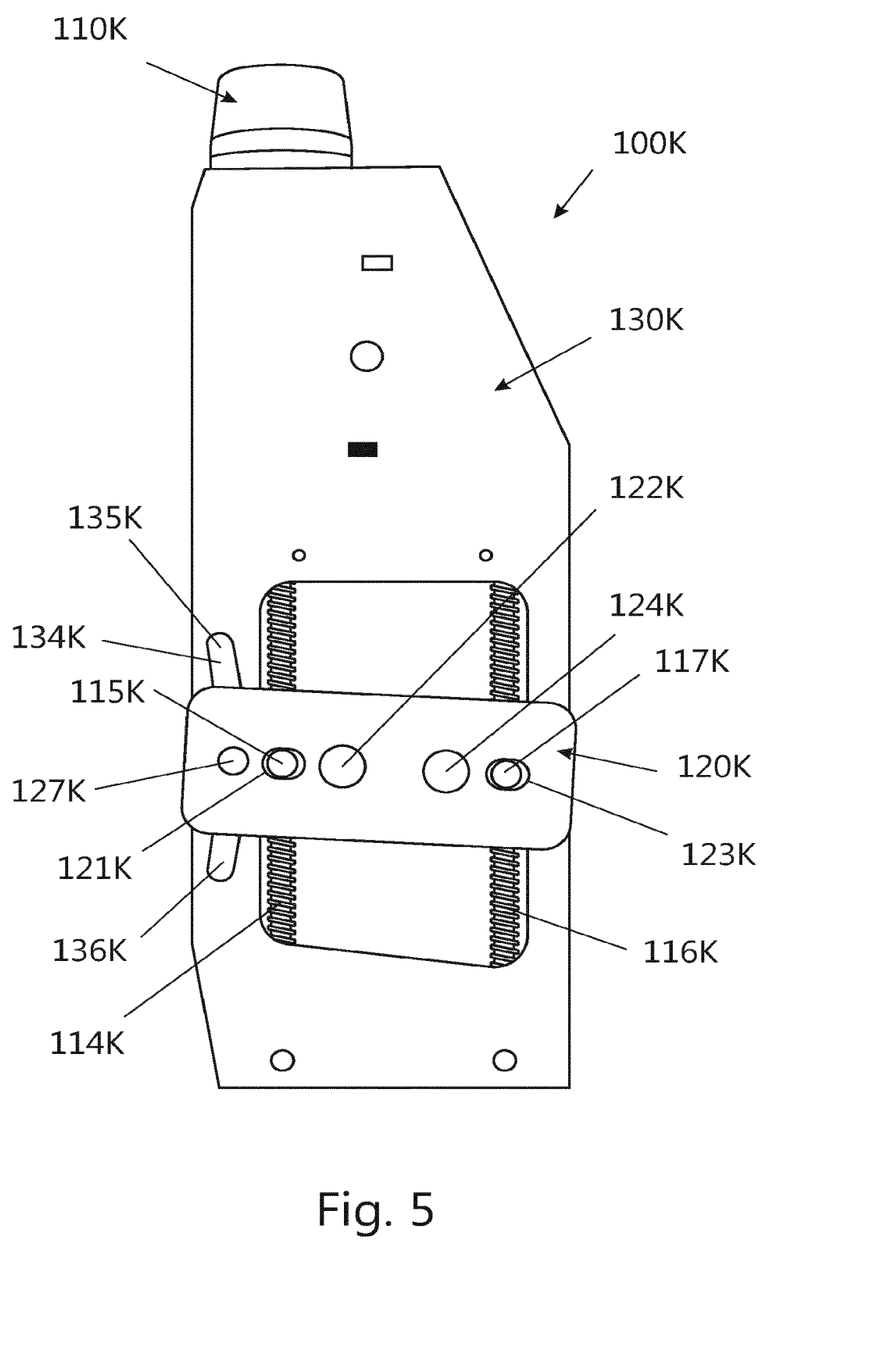
FIG. 5 is an illustration of an adjusting device according to a third embodiment.

FIG. 5 shows an embodiment of an adjusting device 100K, which is similar to the adjusting devices 100A of FIGS. 3a, 3b and 100B of FIG. 4. The adjusting element 110K of the adjusting device 100K comprises a first screw 114K and a second screw 116K for displacing the nail follower 120K, and thus the targeting holes 122K and 124K in a direction substantially parallel to the respective screw axes. The adjusting device 100K differs from the other devices by the arrangement of the first and second screws. According to this embodiment, the screws are not located between the targeting holes. The distance between the targeting holes is smaller than the distance between the screw axes. As shown in FIG. 5, both targeting holes are located between the first and second screws.

Also the nail follower 120K is substantially like the previously described nail followers 120A and 120B. The nail follower 120K additionally comprises a pin 127K. The pin 127K is arranged to engage into a slot 134K in the housing 130K of the adjusting device 100K. It is noted that the slot 134K may extend through the housing, but may also formed like a groove with a bottom surface. Thus, the slot 134K may also be a recess or a groove. Necessary for the intended functionality of the combination of the pin 127K and the slot 134K are curved side surfaces or edges of the slot 134K. These side surfaces are configured to force the pin and thus the nail follower 120K in a direction perpendicular to the axes of the screws 114K and 116K, when the screws act on the nail follower so as to move the same in a direction of the screw axes.

In the embodiment shown in FIG. 5, the slot 134K extends substantially in the dame direction as the longitudinal axis of the screw 114K, 116K, with an upper end 135K and a lower end 136K of the slot being arranged closer to the side of the housing 130K of the adjusting device 100K, i.e. further from the screw 114K, and the mid-section of the slot being arranged more towards a center of the housing, i.e. closer to the screw 114K. The slot 134K is formed with a continuous curvature between the upper and lower ends 135K, 136K. It will be understood that the slot may also have any other appropriate contour, for example with a straight intermediate section or with differing radius of the curvature. It may also be possible that the slot includes sections with reversed curvatures. Pins 115K and 117K are threadably mounted on screws 114K and 116K respectively and move along the threaded shafts as the screws are rotated. The nail follower 120K includes a pair of elongated holes 121K and 123K for respectively receiving pins 115K and 117K. The elongated holes 121K and 123K allow nail follower 120K to move in a direction generally perpendicular to the longitudinal axis of screws 114K and 116K as pin 127K moves along the slot 134K.

Although not explicitly shown, a slot like that shown in the embodiment of FIG. 5 may also be provided in any of the other shown and described embodiments.

Figure 6:
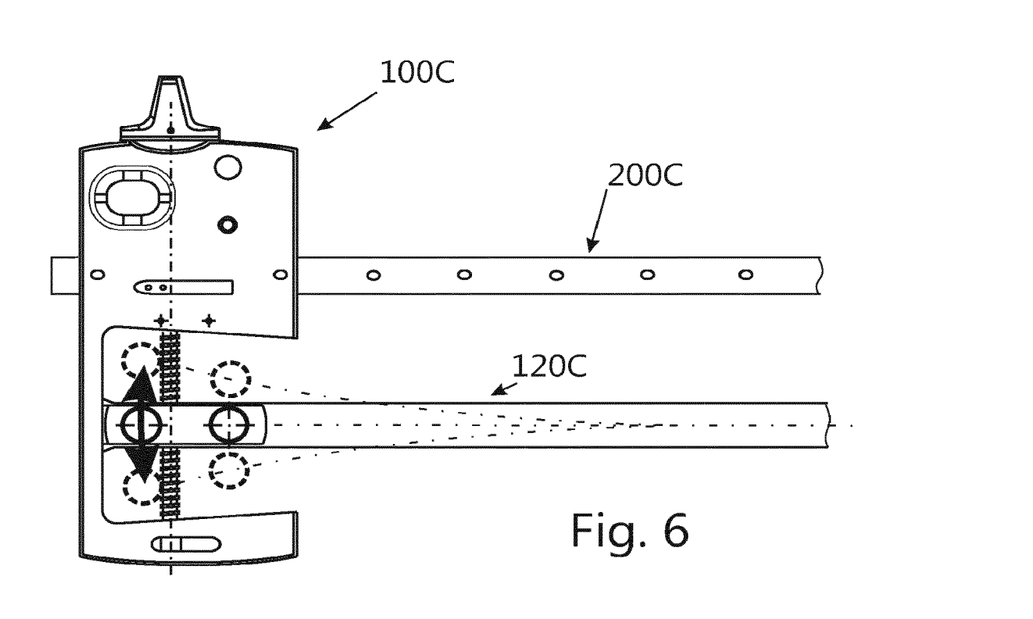
FIG. 6 is an illustration of an adjusting device according to a fourth embodiment.

FIG. 6 shows another embodiment of an adjusting device 100C mounted on a distal targeting arm 200C, the adjusting device having a nail follower 120C which is formed as a bendable or deflectable beam. By means of one screw as an adjusting element it is possible to deform the bendable beam, i.e. the nail follower 120C so as to have a curved distal end portion. Such bending is indicated by the dotted lines denoting the axis of the nail follower 120C in the respective condition. Consequently, the first targeting hole is displaced by a greater length than the second targeting hole.

Figure 7:
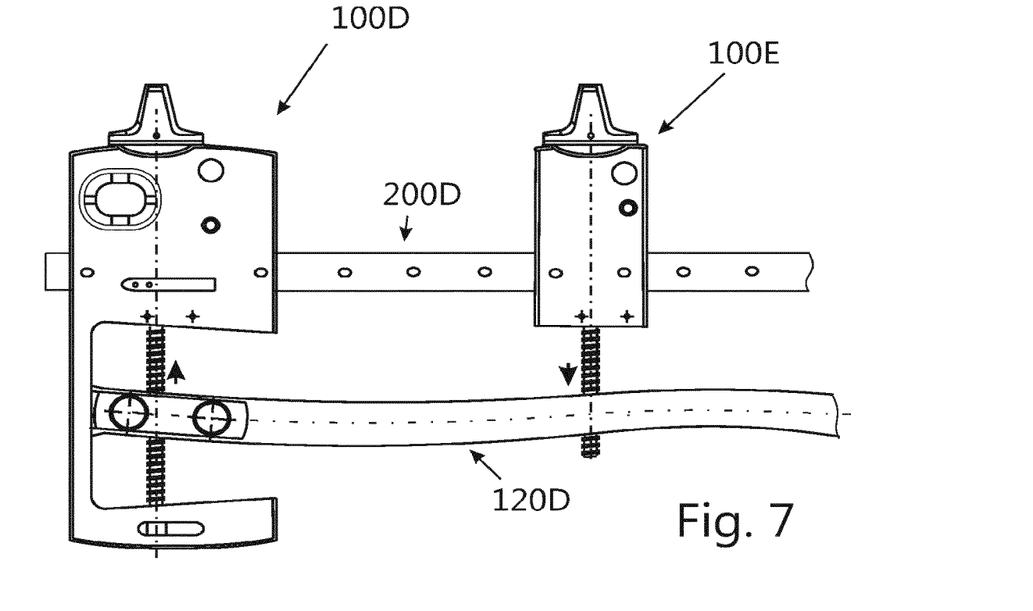
FIG. 7 is an illustration of an adjusting device according to a fifth embodiment.

A further embodiment is shown in FIG. 7, including a further adjusting device 100E. Having both adjusting devices 100D and 100E being mounted on the targeting arm 200D, but at different positions relative to the nail follower 120D, which is also in this embodiment formed as a bendable beam, a complex bending of the nail follower may be possible. The adjusting element of the further adjusting device 100E may engage in a screw-nut (not shown) which may be provided in or at the nail follower 120D, with the screw-nut being pivotable relative to the nail follower so as to allow a continuous bending of the nail follower along its length and past the adjusting element of the adjusting device 100E.

This embodiment may take into account that an intramedullary nail may come in contact at different locations of the medullary channel with the inner bone tissue and forces may apply accordingly on different sections of the nail. As shown in FIG. 7, the mid-portion of the nail follower 120D may be pressed downwardly whereas the distal end portion is pulled upwardly, as indicated by the two arrows in FIG. 7.

It will be understood that even more than two adjusting devices may be provided along the nail follower.

Figure 8:
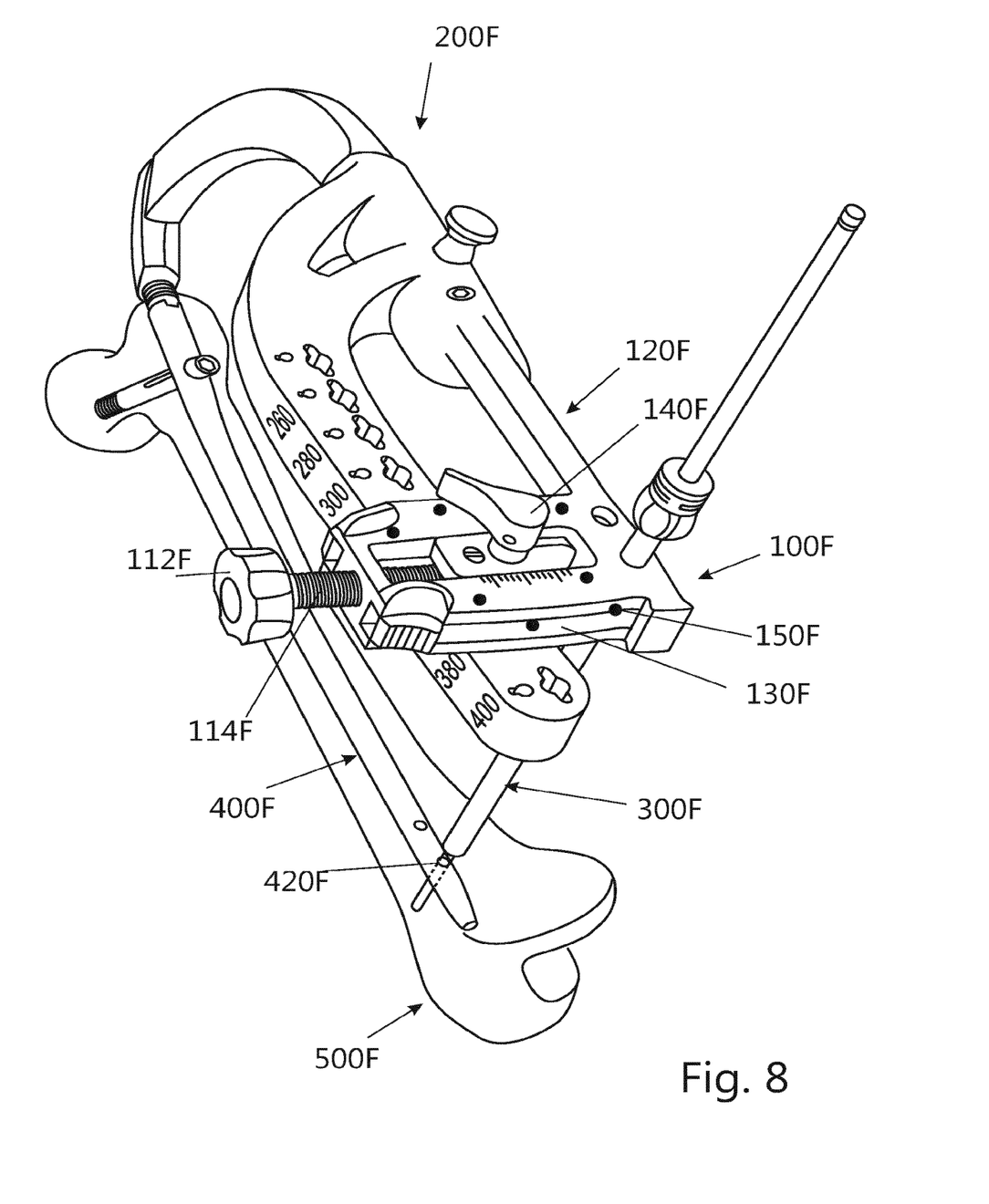
FIG. 8 is an isometric view of an adjusting device according to a sixth embodiment.

FIG. 8 illustrates yet another embodiment of the targeting device comprising an adjusting device 100F with a nail follower 120F formed as an elongated beam. A first end of the nail follower may be coupled to or integrally formed with a proximal portion of the targeting arm 200F, whereas the second end of the nail follower may be adjustably coupled to a distal portion of the targeting arm. Here, the adjusting device 100F comprises an attachment element 140F with a lever allowing a quick-fastening of the adjusting device at the distal portion of the targeting arm. It will be understood that a slight pivot movement of the housing 130F relative to the attachment element 140F should be allowed as the distal portion of the nail follower 120F will tilt as soon as the bendable beam will be bent. The adjusting device according to this embodiment comprises only one screw 114F with a knob 112F as an adjusting element.

Exemplarily, the housing 130F is provided with fiducial markers formed as radio-opaque balls 150F. A plurality of such radio-opaque markers with a specific distribution allows a determination of a 3D-orientation of the housing based on a 2D x-ray image. Consequently, a determination of a viewing angle or a position of one element relative to another element, for example as described in conjunction with FIGS. 10a to 10c, may be performed based on a single x-ray image.

Figure 9:
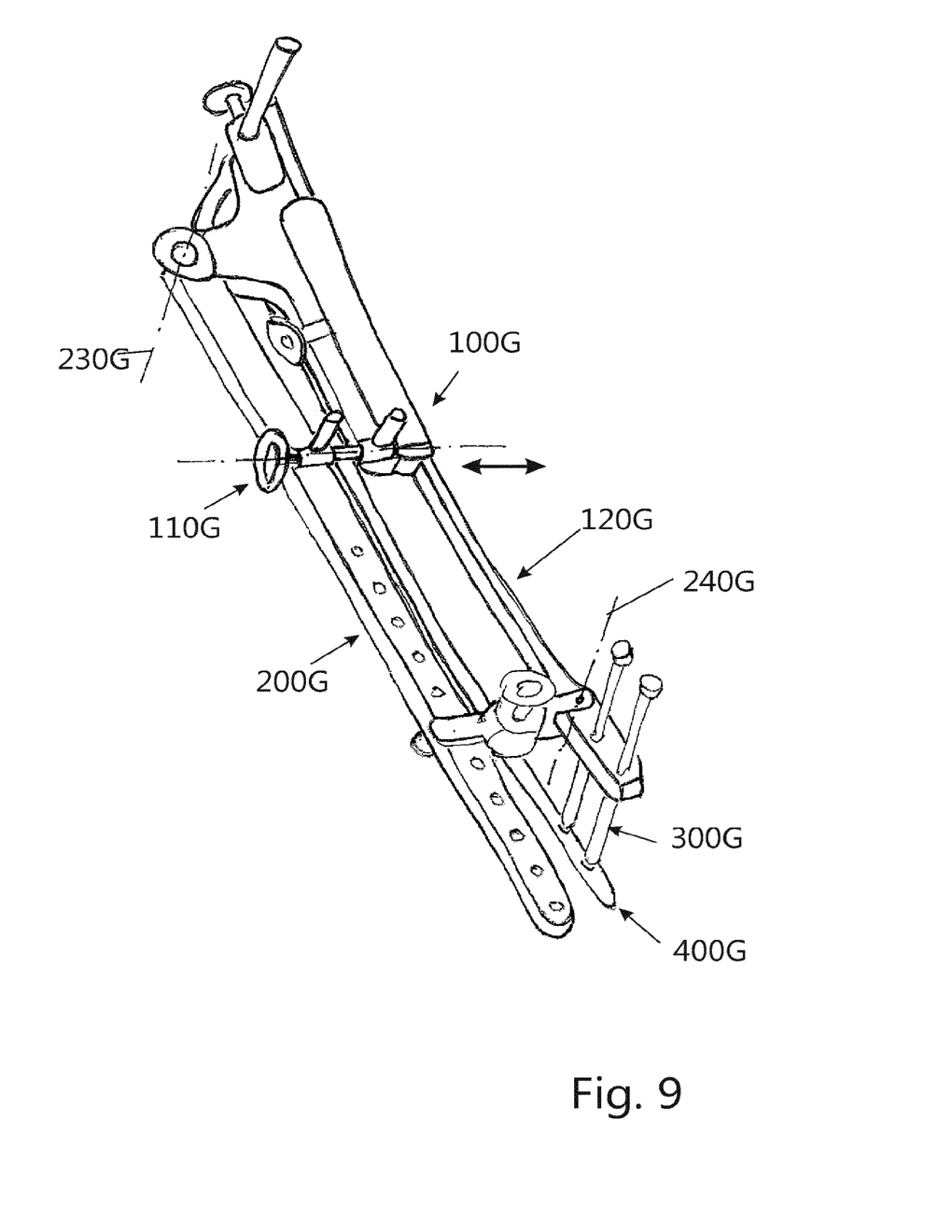
FIG. 9 is an isometric view of an adjusting device according to a seventh embodiment.

FIG. 9 illustrates another embodiment including a bendable nail follower 120G, allowing to adjust the positions of sleeve assemblies 300G so as to be aligned with locking holes in an intramedullary nail 400G. Here, the nail follower is coupled to the distal targeting arm 200G at both end portions of the nail follower. Further, the adjusting device 100G is arranged in a middle section between the two end portions. Operating the adjusting element 110G may push or pull the middle section of the nail follower and thus bend the same.

The nail follower 120G may be coupled to the targeting arm by means of pins each providing a pivot axis. This may allow a continuous bending of the nail follower beyond the pivot axes, when the adjusting element 110G is operated.

Figure 10A:
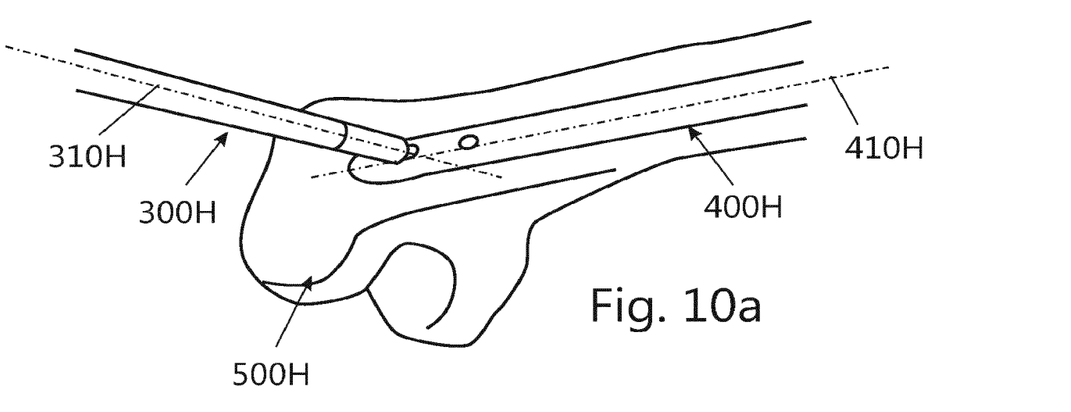
FIGS. 10a to 10c are schematic illustrations of x-ray images generated during a method.
Figure 10B:
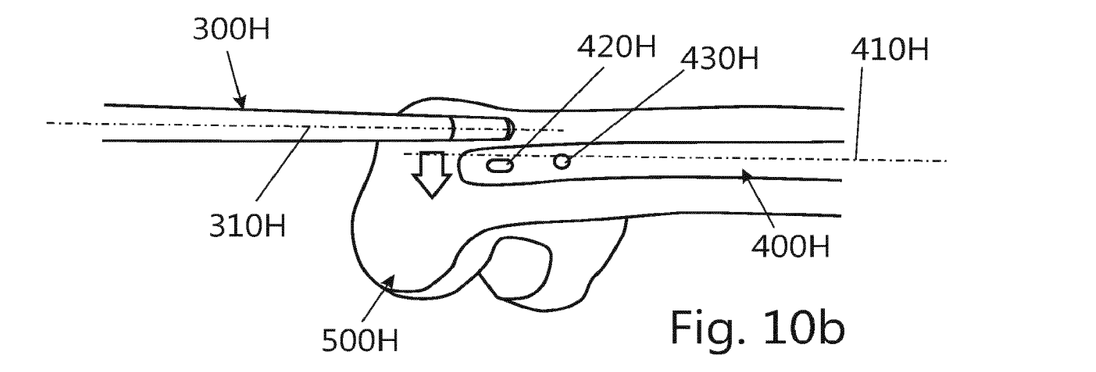
Figure 10C:
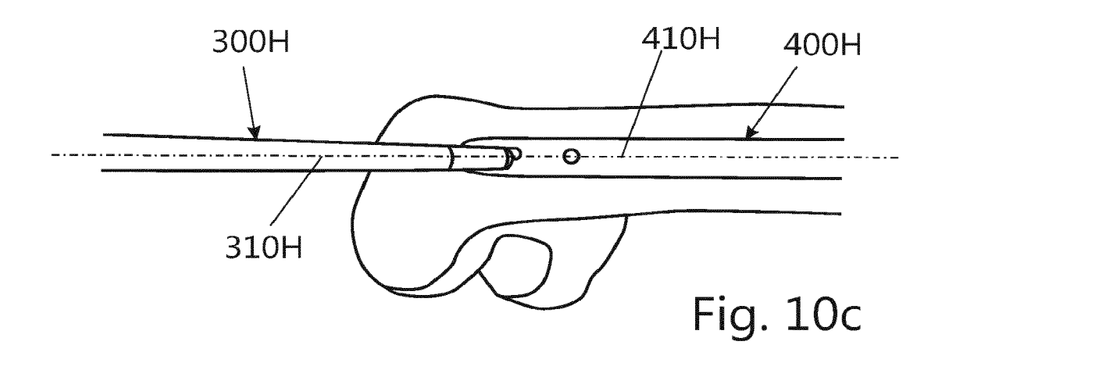

FIGS. 10a to 10c show a series of sketches schematically illustrating a sequence of stages during a process of adjusting a screw axis relative to a bore axis. It is noted that for reasons of clear view the targeting system and in particular the adjusting device is omitted in the sketches of these figures.

In the stage of FIG. 10a, a first x-ray image has been generated showing the distal end portion of the intramedullary nail 400H inside a bone 500H, i.e. a femur. Also visible is a sleeve assembly 300H. In this image, the axis 410H of the intramedullary nail 400H is inclined relative to the axis 310H of the sleeve assembly 300H. Based on one image like that of FIG. 10a, or based on more than one image if necessary, a position and orientation of an imaging device may be determined. Particularly, the position and orientation of an imaging device relative to the imaged structures may be determined based on a single x-ray image when this image includes a visualization of a reference body formed by a plurality of radio-opaque markers with a specific distribution.

Knowing the position and orientation of the imaging device allows for an adjustment of the imaging device to generate an x-ray image within the plane defined by the axis of the intramedullary nail and the axis of the sleeve assembly.

In the stage of FIG. 10b, an image has been generated within the plane defined by the two axes 310H and 410H. As a result, these axes extend parallel to each other, as shown in the figure. The intramedullary nail 400H is illustrated with a distal end portion being slightly bent downwardly. Consequently, the axis 410H of the nail 400H is considered as a main axis which is nevertheless straight so that the first locking hole 420H and the second locking hole 430H are not anymore located on this axis. On the other hand, this straight axis may define a plane together with the axis of the sleeve assembly.

In the stage of FIG. 10c, the position of the sleeve assembly 300H has been adjusted so that the axis 310H of the sleeve assembly is aligned with the axis of the first locking hole in the nail.

Figure 11:
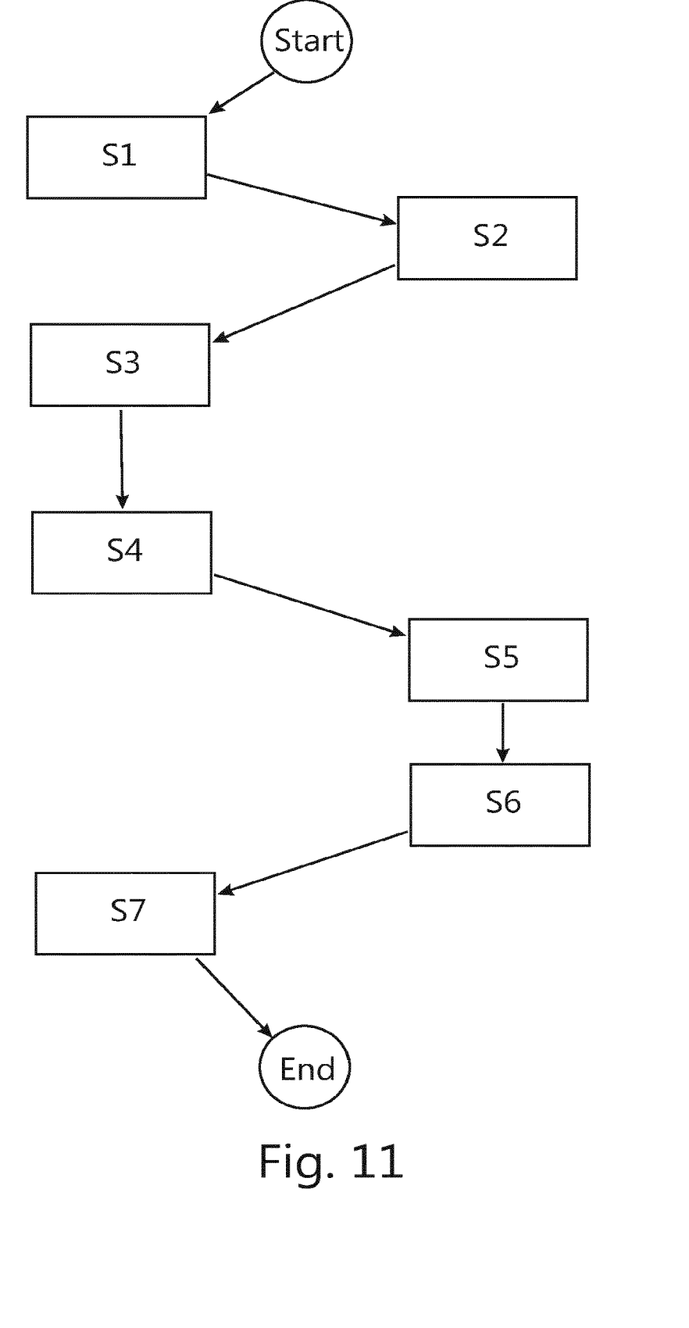
FIG. 11 is a flowchart representing method steps.

The flow-chart in FIG. 11 illustrates the principles of using or operating the targeting device. It will be understood that the described steps are major steps, wherein these major steps might be differentiated or divided into several sub-steps. Furthermore, there might be also sub-steps between these major steps.

The schematically illustrated methods start at the circle denoted with 'start'.

In step S1, a first end of the targeting arm is coupled with an intramedullary nail which is already inserted into a medullary channel of a bone.

In step S2, the adjusting device is coupled to the distal portion of the targeting arm. The position at the targeting arm depends on the configuration of the intramedullary nail, i.e. depends on the position of the locking holes in the distal end portion of the intramedullary nail.

In step S3, a first x-ray image is generated with an imaging direction being inclined both relative to the nail axis as well as to the axis of anyone of the targeting holes.

In step S4, the imaging direction is adjusted so that this direction lies within a plane defined by the nail axis and at least one of the targeting hole axes. Furthermore, the imaging direction is adjusted so as to be between 20 and 40 degrees, in particular 30 degrees inclined relative to the targeting hole axes, i.e. so as to be between 50 and 70 degrees, in particular 60 degrees inclined relative to the nail axis.

In step S5, a second x-ray image is generated allowing a determination of a deviation of the distal portion of the intramedullary nail, in particular of a first and a second locking hole from an expected position due to a bending of this portion of the nail.

In step S6, the adjusting element of the adjusting device is operated so as to displace the targeting holes correspondingly, i.e. according to the determined deviation.

In step S7, the correct alignment of the axis of the targeting hole and thus of a sleeve assembly which can be received in the targeting hole, relative to the axis of the related locking hole in the intramedullary nail may be confirmed based on a further x-ray image.

The methods end at the circle denoted with 'end'.

Subsequently, a distal locking screw may be inserted through the locking hole to anchor the bone segment to the bone nail.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

LIST OF REFERENCE SIGNS

It is noted that characters like 'A', 'B' or 'C' behind a reference numeral should be considered as indices which may serve to differentiate embodiments of different figures.
100 adjusting device
110 adjusting element
112 knob
114 first screw
115 screw pin
116 second screw
117 screw pin
118 gear
120 nail follower
121 elongated hole
122 first targeting hole
123 elongated hole
124 second targeting hole
126 nail follower body
127 slot pin
128 nail follower member
130 housing
132 groove
134 slot
135 upper slot end
136 lower slot end
140 attachment element
200 distal targeting arm
210 first end
220 receipt for adjusting device
230 first pivot axis
240 second pivot axis
300 sleeve assembly
310 axis of sleeve assembly

The invention claimed is:

1. A targeting system for a bore in a distal end portion of an intramedullary nail, comprising:
    a distal targeting arm having a first end configured to be coupled to a trailing end of an intramedullary nail,
    an adjusting device configured to be coupled to the distal targeting arm, wherein the adjusting device comprises an adjusting element and a nail follower including two targeting holes configured to receive a sleeve assembly, wherein the adjusting element engages the nail follower and is configured to adjust the position of the nail follower so that the targeting holes correspond to respective locking holes at a leading end of the intramedullary nail, when the nail is bent, and
    wherein the adjusting element comprises two screws coupled by a gear with a gear ratio different from 1:1.

2. The targeting system of claim 1, wherein at least one of the screws has a thread which engages with a threaded hole in the nail follower.

3. The targeting system of claim 1, wherein the adjusting element comprises a first screw including a first thread with a first pitch and a second screw including a second thread with a second pitch different from the first pitch.

4. The targeting system of claim 1, wherein the adjusting element comprises two screws with equal pitches.

5. The targeting system of claim 1, wherein a first one of the two screws rotates in an opposite direction relative to a second one of the two screws, when the adjusting element is operated.

6. The targeting system of claim 1, wherein a first threaded bore in the nail follower is arranged adjacent to a first one of the two targeting holes and a second threaded bore in the nail follower is arranged adjacent to a second one of the two targeting holes, the axes of the threaded bores being oriented transverse to the axes of the targeting holes.

7. The targeting system of claim 1, wherein the adjusting device further comprises a cam mechanism, and wherein the cam mechanism engages the nail follower and is configured to cooperate with the adjusting element to adjust the position of the nail follower.

8. The targeting system of claim 1, wherein the nail follower comprises a first member including a first one of the targeting holes and a second member including a second one of the targeting holes, and wherein the first member and the second member are movable relative to each other.

9. The targeting system of claim 1, wherein the nail follower is configured to be deformed.

10. The targeting system of claim 1, wherein the position of a first one of the targeting holes is displaced by a first length and the position of the second one of the targeting holes is displaced by a second length, when the adjusting element is operated, and wherein the first length is 8 to 12 percent larger than the second length.

11. The targeting system of claim 1, wherein the adjusting device further comprises a housing including a plurality of radio-opaque markers with a distribution configured for determining a 3D-orientation of the housing based on a 2D x-ray image.

12. A targeting system for a bore in a distal end portion of an intramedullary nail, comprising: a distal targeting arm with a first end being configured to be coupled to a trailing end of an intramedullary nail, an adjusting device, the adjusting device being configured to be coupled to the distal targeting arm, wherein the adjusting device comprises an adjusting element and a nail follower including a plurality of targeting holes each being configured to receive a sleeve assembly, wherein the adjusting element engages the nail follower and is configured to adjust the position of the nail follower so that the targeting holes correspond to respective locking holes at a leading end of the intramedullary nail, when the nail is bent, and wherein the adjusting element comprises a plurality of screws each extending entirely through the nail follower, and wherein a first one of the plurality of screws of the adjusting element includes a first threat with a first pitch and a second one of the plurality of screws includes a second thread with a second pitch different from the first pitch.

13. The targeting system of claim 12, wherein at least one of the plurality of screws has a thread which engages with a threaded hole in the nail follower.

14. The targeting system of claim 12, wherein both of the screws of the adjusting element extend between the targeting holes of the nail follower.

15. The targeting system of claim 12, wherein a first one of the plurality of screws rotates in an opposite direction relative to a second one of the plurality of screws, when the adjusting element is operated.

16. The targeting system of claim 12, wherein a first threaded bore in the nail follower is arranged adjacent to a first one of the targeting holes and a second threaded bore in the nail follower is arranged adjacent to a second one of the targeting holes, the axes of the threaded bores being oriented transverse to the axes of the targeting holes.

17. The targeting system of claim 12, wherein the position of a first one of the targeting holes is displaced by a first length and the position of the second one of the targeting holes is displaced by a second length, when the adjusting element is operated, and wherein the first length is 8 to 12 percent larger than the second length.

18. A targeting system for a bore in a distal end portion of an intramedullary nail, comprising:
 a distal targeting arm with a first end being configured to be coupled to a trailing end of an intramedullary nail,
 an adjusting device, the adjusting device being configured to be coupled to the distal targeting arm, wherein the adjusting device comprises an adjusting element and a nail follower including a plurality of targeting holes each being configured to receive a sleeve assembly,
 wherein the adjusting element engages the nail follower and is configured to adjust the position of the nail follower so that the targeting holes correspond to respective locking holes at a leading end of the intramedullary nail, when the nail is bent,
 wherein the adjusting element comprises a plurality of screws each extending entirely through the nail follower, and
 wherein the plurality of screws are coupled by a gear with a gear ratio different from 1:1.

19. The targeting system of claim 18, wherein the plurality of screws have equal pitches.

20. The targeting system of claim 18, wherein both of the screws of the adjusting element extend between the targeting holes of the nail follower.

\* \* \* \* \*